United States Patent [19]

Fogarty

[11] Patent Number: 4,821,719
[45] Date of Patent: * Apr. 18, 1989

[54] COHESIVE-ADHESIVE ATRAUMATIC CLAMP

[76] Inventor: Thomas J. Fogarty, 770 Welch Rd., Suite 216, Palo Alto, Calif. 94304

[*] Notice: The portion of the term of this patent subsequent to Sep. 9, 2003 has been disclaimed.

[21] Appl. No.: 898,313

[22] Filed: Aug. 20, 1986

Related U.S. Application Data

[63] Continuation-in-part of Ser. No. 677,561, Dec. 3, 1984, Pat. No. 4,611,593.

[51] Int. Cl.⁴ .................................................. A61B 17/12
[52] U.S. Cl. ...................................... 128/325; 128/322; 128/327
[58] Field of Search ............... 128/325, 327, 322, 346, 128/321

[56] References Cited

U.S. PATENT DOCUMENTS

| | | | |
|---|---|---|---|
| 2,743,726 | 5/1956 | Grieshaber | 128/322 |
| 3,503,396 | 3/1970 | Pierie et al. | 128/322 |
| 3,503,398 | 3/1970 | Fogarty et al. | 128/346 |
| 3,746,002 | 7/1973 | Haller | 128/322 |
| 4,611,593 | 9/1986 | Fogarty et al. | 128/325 |

Primary Examiner—Gene Mancene
Assistant Examiner—Cary E. Stone
Attorney, Agent, or Firm—Limbach, Limbach & Sutton

[57] ABSTRACT

Replaceable cohesive-adhesive pads are provided for vessel occluding devices of both the tie-on and jaw-clamp types. When applied to an anatomical vessel the pads act collectively with the fibrous surface of the vessel to produce an adherence relationship therewith. The pads are shown secured in place through either sleeve-like connections, or button-headed connector which snap into secure engagement with undercut recesses.

13 Claims, 1 Drawing Sheet

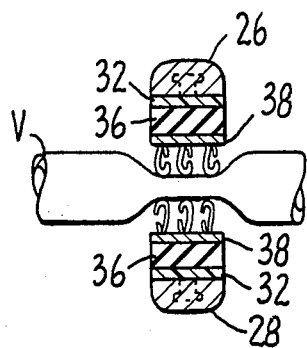
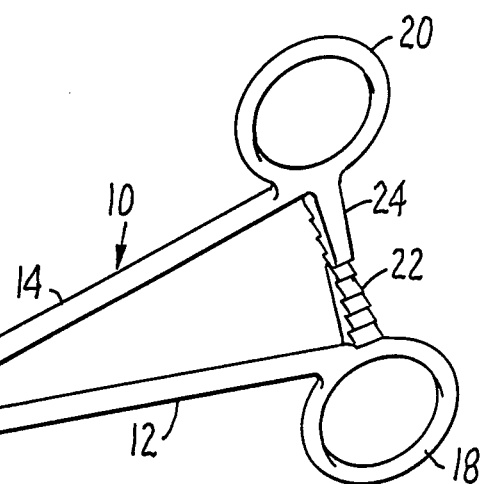
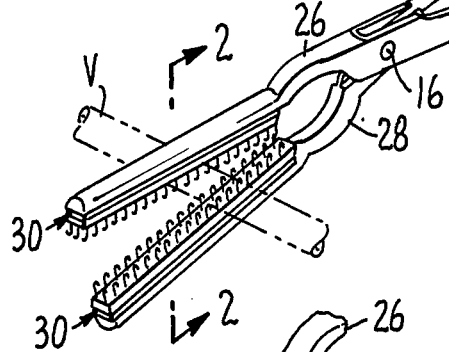
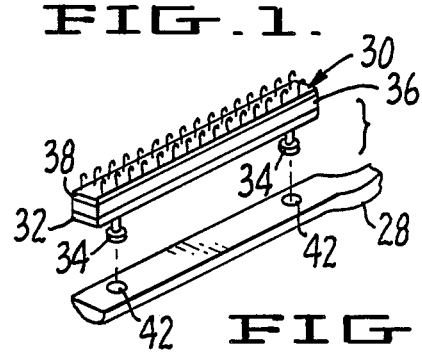
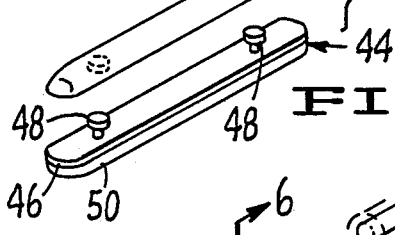
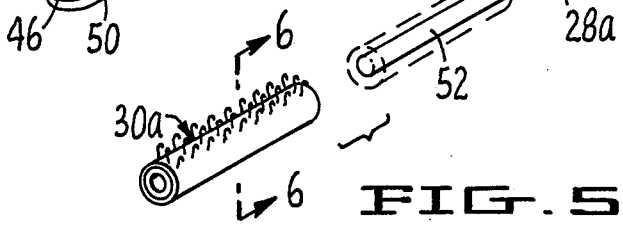
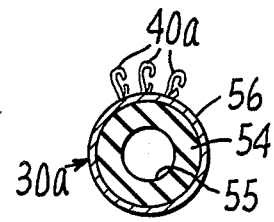
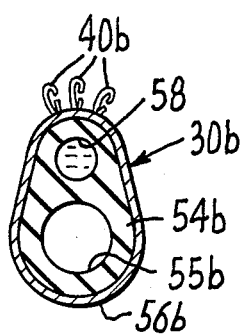
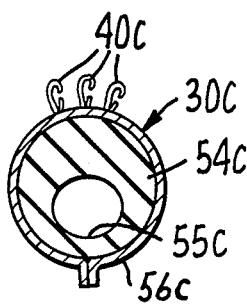
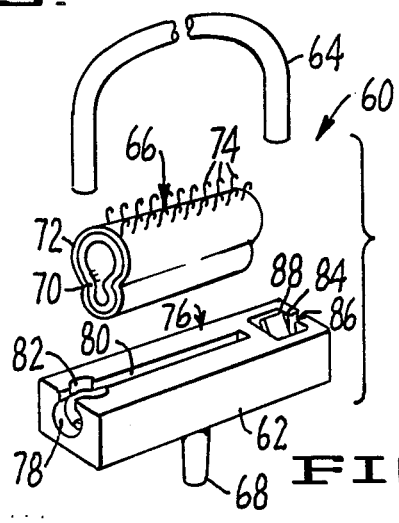

COHESIVE-ADHESIVE ATRAUMATIC CLAMP

RELATED APPLICATION

This application is a continuation-in-part of copending application Ser. No. 677,561 filed Dec. 3, 1984 for an invention entitled "VESSEL OCCLUDING INSTRUMENT" now U.S. Pat. No. 4,611,593.

BACKGROUND OF THE INVENTION

The present invention relates to a vessel occluding instrument and, more particularly, to such an instrument which is provided with a cohesive-adhesive pad which acts collectively with the fibrous surface of an anatomical vessel to produce an adherent relationship therewith.

Atraumatic instruments for occluding blood vessels during arterial reconstructive surgery have been used for many years. The ideal instrument should provide not only occlusive forces on the vessel, but also sufficient traction to facilitate the surgical procedure. Since vessels come in various dimensions and with different physical conditions, the ideal occluding instrument should be capable of readily adjusting to these variables. For example, the occluding portions of the instrument should be capable of deforming readily to accommodate the irregular shapes of atherosclerotic plaques which are attached to the interior surfaces of vessels. This deformation capability also permits the occluding instrument to clamp over indwelling catheters which are used for dilatation, irrigation, aspiration and infusion of vessels during reconstructive procedures. Moreover, the ideal occluding instrument should be not only easy to apply and remove from vessels, but also sufficiently small in size as to not obstruct the operative field.

The prior art devices of U.S. Pat. Nos. 3,880,166 and 3,993,076 are designed for the gentle occluding of anatomical vessels during surgery. While these patents have similarities to certain embodiments of the present invention, they do not embody cohesive-adhesive pads of the type with which the present invention is concerned. The device of aforementioned copending application Ser. No. 677,561 embodies such a pad, but is not removable, or designed for use with jaw-type occluding instruments.

U.S. Pat. Nos. 3,503,396, 3,503,397 and 3,503,398 all disclose jaw-type atraumatic surgical clamps with replaceable cushioned inserts which are designed to gently and effectively clamp an anatomical vessel. These cushions, however, are not of a cohesive-adhesive character which acts collectively with the fibrous surface of the vessel to produce an adherence relationship therewith.

SUMMARY OF THE INVENTION

The instrument of the present invention has as its base element an elongated generally rigid body member having top and bottom surfaces. A resilient pad having a cohesive-adhesive cover is secured to the bottom surface of the body member and provides means which functions collectively with the fibrous surface of an anatomical vessel to collectively produce a coherent relationship therewith. Clamp means is secured to the body member in apposition to the bottom surface to selectively draw a vessel into adherence relationship with the cover.

A principal object of the invention is to provide a vessel occluding instrument with a cohesive-adhesive surface capable of producing an adherence relationship with the fibrous surface of an anatomical vessel.

Another object of the invention is to provide such an instrument wherein the cohesive-adhesive surface provides a resilient pad.

Yet another object of the invention related to the latter object is to provide such an instrument wherein the resilient pad is releasably secured in place and may be readily replaced.

Still another object of the invention is to provide such an instrument employing a relatively conventional jaw clamp.

A further object of the invention is to provide such an instrument of the jaw clamp type wherein the cohesive-adhesive surface may be provided on one or both jaws of the clamp.

Still another object of the invention is to provide such an instrument of the jaw clamp type wherein one jaw of the clamp is provided with a cohesive-adhesive surface and the other jaw is provided with a relatively smooth resilient surface.

Yet a further object of the invention is to provide such an instrument of the type shown in copending application Ser. No. 677,561 wherein improved means is provided for securing the resilient pad to the body member of the instrument.

These and other objects will become more apparent when viewed in light of the accompanying drawings and following detailed description.

BRIEF DESCRIPTION OF THE DRAWINGS

FIG. 1 is a perspective view of a first embodiment jaw-type occluding instrument embodying the present invention, with phantom lines showing an anatomical vessel in the process of being clamped by the instrument;

FIG. 2 is a cross-sectional elevational view taken on the plane designated by line 2—2 of FIG. 1, with solid lines showing a vessel clamped by the instrument;

FIG. 3 is an exploded perspective view of the lower jaw of the instrument shown in FIG. 1, illustrating the manner in which the cohesive-adhesive resilient pad is releasably secured to the jaw.

FIG. 4 is an exploded perspective view illustrating a smooth surfaced resilient pad which may be secured to the upper jaw of the FIG. 1 instrument in place of the cohesive-adhesive resilient pad;

FIG. 5 is an exploded perspective view of the lower jaw of a jaw-type clamp provided with the cohesive-adhesive resilient pad of the present invention wherein the pad is secured to the jaw through means of a sleeve connection;

FIG. 6 is a cross-sectional elevational view taken on the plane designated by line 6—6 of FIG. 5;

FIG. 7 is a cross-sectional elevational view similar to FIG. 6, illustrating an alternative sleeve connection for the resilient pad wherein the connection incorporates an elastomeric pad having a void therein which may be hollow or receive a gel;

FIG. 8 is a cross-sectional elevational view similar to FIG. 6 illustrating another sleeve connection wherein an enlarged uniform density elastomeric cushion is incorporated into the connection; and FIG. 9 is an exploded perspective view of a vessel occluding instrument of the general type shown in aforementioned copending application Ser. No.

677,561, wherein the resilient pad is secured in place through means of a channel connection.

DESCRIPTION OF THE ILLUSTRATED EMBODIMENTS

The instrument of FIG. 1 is designated in its entirety by the numeral 10 and comprises a pair of jaws 12 and 14 hingedly secured together by pin 16. The proximal ends of the jaws are formed with finger and thumb rings 18 and 20, respectively, and interengageable ratchet racks 22 and 24. In conventional manner, the ratchet racks provide means whereby the jaws may be secured in adjusted clamped condition relative to one another. The distal or clamp ends of the jaws are designated by the numerals 26 and 28.

All of the above-described structure of the instrument 10 is relatively conventional. The novelty of the instrument resides in the resilient pads 30 secured to the clamp ends of the jaws. These pads each comprise: a resilient backing strip 32 of a tough high density polymer, such as nylon; a pair of button head protrusions 34 fixedly secured to and extending from the backing strip in spaced relationship to one another; an elastomeric cushion 36 secured to and extending over the length of the backing strip 32; and, a cohesive-adhesive cover sheet 38 secured to and extending over the length of the cushion 36. The sheet 38 has Velcro-like loops secured to and extending from it outer surface. These loops are capable of interacting with the external adventitial layer of a blood vessel to create an adherence relationship therewith similar to the bonding of Velcro materials. Such a vessel is shown in FIGS. 1 and 2 and designated by the letter "V". The adherence relationship is the result of the collective interaction of the Velcro-like loops with the fiber-like surface of the vessel. It improves traction between the instrument 10 and vessel "V" by preventing slipping between the two.

The manner by which the pads 30 are secured to the clamp ends 26 and 28 is illustrated in FIG. 3. There it can be seen that the clamp end 28 is formed with a pair of undercut recesses 42 disposed for alignment with the button head protrusions 34. The recesses are of a diameter sufficient to receive the heads of the protrusions 34 and are actually spaced by a distance just slightly greater than the distance between the opposed surfaces of the button heads on the respective protrusions. Thus, the protrusions cannot enter the recesses without spreading slightly. The respective recesses are undercut so that once the protrusions are in place within the recesses, the button heads on the protrusions snap beneath the undercut edges of the recesses. With the button heads so disposed, the pads 30 are releasably secured against inadvertent removal from the clamp ends.

As shown in FIGS. 1 and 2, both of the clamp ends of the instrument are provided with pads 30 having cover sheets 38 with Velcro-like loops. Thus, this embodiment produces a cohesive-adhesive relationship with both sides of a vessel clamped thereby. FIG. 4 shows an alternative embodiment wherein the clamp end 26 is provided with a resilient pad 44 having a smooth outer surface. The pad 44 comprises a resilient backing strip 46 similar to the strip 32 having button head protrusions 48 similar to the protrusions 34. A smooth resilient cushion 50 is secured to and extends over the full length of the backing strip 46. The protrusions 48 are received in recesses (not illustrated) in the clamp end 26, similarly to the manner in which the protrusions 34 are received in the recesses 42.

FIG. 5 shows an alternative embodiment jaw-type occluding instrument wherein the resilient pad is secured in place by a sleeve connection. Although not illustrated, it should be understood that the jaw-type clamp would include a pair of opposed jaws similar to those of the FIG. 1 embodiment. The clamp end shown in FIG. 6 is designated by the numeral 28a and is shown as having a distal end section 52 of a generally cylindrical cross-section. The pad of the FIG. 5 embodiment is designated by the numeral 30a and comprises: an elastomeric tube 54 having a passage 55 proportioned for snug slidable receipt over the distal end section 52; a cover sheet 56 extending around the elastomeric tube 54; and Velcro-like loops 40a secured to and extending upwardly from the cover sheet. In use, the embodiment of FIG. 5 co-acts with an anatomical vessel similar to the FIG. 1 embodiment. It should be understood that an upper clamp end of similar construction to the clamp end 28a would be disposed in apposed relationship to the clamp end 28a.

FIG. 7 shows a variation of the FIG. 5 resilient pad. The pad of FIG. 7 is designated by the numeral 30b and comprises: an elastomeric tube 54b; a cover sheet 56b; and Velcro-like loops 40b. The tube 54 is formed with cylindrical passage 55b proportioned for snug receipt over the distal end section 52, similarly to what is seen in FIG. 5. A secondary passage 58 extends through the tube 54b in spaced parallel relationship to the passage 55b. The secondary passage provides added resilience to the tube and, if desired, may be filled with a gel-like material.

FIG. 8 illustrates another variation of the resilient pad of the FIG. 5 embodiment. The FIG. 8 pad is designated in its entirety by the numeral 30c and comprises: an elastomeric tube 54c having a cylindrical passage 55c extending longitudinally therethrough; a cover sheet 56c extending around the tube 54c; and Velcro-like loops 40c secured to and extending from the cover sheet.

The variations of FIG. 7 and 8 are applied and operate in the same manner as the FIG. 5 embodiment. In place, the tubes 54b and 54c would be snugly received around the distal end sections of the jaw elements. The principal difference between the embodiment of FIG. 5 and the embodiments of FIG. 7 and 8 is that the latter embodiments provide additional resilience due to the construction of the elastomeric tubes incorporated therein. Such added resilience in the FIG. 7 embodiment results from the added depth of the tube 54b and the secondary passage 58 incorporated therein. The added resilience in the FIG. 8 embodiment results from the added thickness of the tube 54c and the asymmetrical positioning of the passage 55c therein.

The occluding instrument of FIG. 9 is designated in its entirety by the numeral 60 and comprises: an elongated body member 62; a length of resilient tape 64; a resilient pad 66; and a positioning lug 68. In operation, the instrument 60 functions and is used in a manner identical to that of the instrument shown in aforementioned copending application Ser. No. 677,561. The only difference between the instrument 60 and the instrument of that application is in the construction of the pad 66 and the construction of the body member 62 provided to secure the pad to the member.

The pad 66 comprises: an elongate resilient tube 70 of an hourglass-shaped cross-sectional configuration; a cover sheet 72 extending around and covering the tube 70; and a plurality of Velcro-like loops 74 secured to and extending upwardly from the sheet 72.

The body member 62 is provided with a channel 76 for snug receipt of the lower portion of the pad 66. This channel comprises an enlarged generally cylindrical section 78 extending longitudinally through the greater part of the length of the body member 62 and opening through one end thereof; and a necked down slot 80 opening through the top surface of the body member 62 and communicating with the cylindrical section 78.

The pad 66 is assembled into secure relationship with respect to the member 62 by sliding the lower portion of the hourglass configuration of the pad into the cylindrical section 78, with the intermediate portion of the pad extending through the slot 80 and the upper portion of the pad disposed on the top of the member 62. The pad 66 is of a length shorter than the channel 76 in order to leave a passage 82 which extends through the body member 62 in an unobstructed condition. This passage is provided for snug receipt of one end of the tape 64. A passageway 84 extends through the body member 62 at the end thereof opposite that through which the passage 82 extends. The passageway 84 communicates with a slot 86 opening through the end of the body member and is provided with a tine 88 for locking engagement with the tape 64 when the tape is extended through the passageway. The tape is pulled through the passage 82 and the passageway 84 to provide clamp means to draw an anatomical vessel into engagement with the pad 66. The locking lug 68 provides an element which may be gripped by forceps or the like to aid in locating and positioning the instrument 60.

Conclusion

While preferred embodiments have been illustrated and described, it should be understood that the invention is not intended to be limited to the specifics of these embodiments, but rather is defined by the accompanying claims.

I claim:

1. A vessel occluding instrument for facilitating the treatment of an anatomical vessel, said instrument comprising: an elongated generally rigid body member having top and bottom surfaces; resilient pad means secured to the bottom surface of said body member, said resilient pad means comprising a cohesive-adhesive covering sheet for releasably and atraumatically securing said pad means to said vessel, whereby said sheet and said vessel collectively produce an adherence relationship therebetween; and clamp means secured to said body member in apposition to the bottom surface thereof to selectively draw said vessel into adherence relationship to the covering sheet of said resilient pad means.

2. A vessel occluding instrument according to claim 1 wherein said rigid body member comprises a first jaw and the clamp means comprises a second jaw hingedly secured to said first jaw for movement towards and away therefrom.

3. A vessel occluding instrument according to claim 2 wherein said second jaw has a top surface in apposition to the first jaw, said instrument further comprising a cohesive-adhesive covering sheet on said top surface for releasably and adhesively engaging said vessel upon drawing of said vessel into adherence relationship to the covering sheet of said first jaw by said second jaw.

4. A vessel occluding instrument according to claim 2 wherein said second jaw has a top surface in apposition to the first jaw, said instrument further comprising a resilient cushion on said top surface for engagement with said vessel upon drawing of said vessel into adherence relationship to the covering sheet of said first jaw by said second jaw.

5. A vessel occluding instrument according to claim 1 wherein the resilient pad is releasably secured to the body member by a structure comprising: an elongate channel formed in the body member, said channel having an enlarged section within the body member and a convergent section opening through said bottom surface; an elongate bead carried by the resilient pad, said bead being received within said enlarged section and being of a cross-section greater than that of said convergent section; and an opening at one end of said channel to provide for passage of said bead into and out of said enlarged section.

6. A vessel occluding instrument according to claim 1 wherein said resilient pad is releasably secured to the body member by a sleeve attached thereto and proportioned for snug slidable receipt over the body member.

7. A vessel occluding instrument according to claim 6 wherein said sleeve includes an elastomeric cushion so disposed as to be positioned between said pad and bottom surface upon receipt of the sleeve over the body member.

8. A vessel occluding instrument according to claim 7 wherein said elastomeric cushion includes a gel filled chamber.

9. A vessel occluding instrument according to claim 1 wherein the resilient pad is releasably secured to the body member by structure comprising: a resilient backing strip affixed to the pad; at least one pair of buttonhead protrusions fixed to and extending from said backing strip; and a pair of sockets formed in the bottom surface of the body member, said sockets being proportioned for receipt of said protrusions and positioned and undercut for simultaneous engagement thereover.

10. A vessel occluding instrument according to claim 9 further comprising an elastomeric cushion interposed between said pad and backing strip.

11. A surgical clamp comprising a pair of opposed jaws operatively connected together for movement towards each other to clamp an anatomical vessel therebetween, at least one of said jaws having resilient pad means secured thereto for engagement with a vessel clamped between the jaws, said pad means having a cohesive-adhesive surface for releasably and atraumatically securing said pad means to a vessel clamped between said jaws whereby said surface and vessel produce an adherence relationship therebetween.

12. A clamp according to claim 11 wherein the jaw opposite said one jaw is provided with resilient pad means for engagement with a vessel clamped between said jaws.

13. A surgical clamp comprising a pair of jaws connected together for movement towards and away from each other, said jaws having opposed clamping surfaces; and resilient pad means secured to said surfaces for engagement with the opposite sides of a anatomical vessel clamped therebetween, said resilient pad means having cohesive-adhesive surfaces for releasably and atraumatically engaging a vessel clamped between said jaws whereby said surfaces produce an adherence relationship with opposite sides of said vessel.

* * * * *